United States Patent
Forster

(12) 
(10) Patent No.: US 6,274,569 B1
(45) Date of Patent: Aug. 14, 2001

(54) PESTICIDAL COMPOSITIONS

(75) Inventor: Birgit Forster, Riehen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/531,370

(22) Filed: Mar. 21, 2000

(30) Foreign Application Priority Data

Mar. 23, 1999 (GB) .................................... 9906691

(51) Int. Cl.$^7$ .......................... A01N 55/00; A01N 43/36; A01N 43/54
(52) U.S. Cl. ............................ 514/63; 514/260; 514/422
(58) Field of Search ................................ 514/422, 63, 260

(56) References Cited

PUBLICATIONS

The Pesticide Manual, 10th ed., 1994, 326.
The Pesticide Manual, 10th ed., 1994 338.
Tomlin, The Pesticide Manual Incorporating The Agrochemicals Handbook, 10th ed. (1995) pp. 482,483,498 and 499.*
Beale et al, Proceedings Brighton Conference, (1998) pp. 343–350.*
Database CROPU Online No. 1999–82913 (1998).

* cited by examiner

Primary Examiner—Allen J. Robinson
(74) Attorney, Agent, or Firm—William A. Teoli, Jr.

(57) ABSTRACT

An agrochemical composition, comprising at least two active ingredient components together with a suitable carrier, wherein component I is I) fludioxonil (=4-(2,2-difluoro-1,3-benzodioxol-4-yl) pyrrole-3-carbonitrile) and wherein component II is IIA) fluquinconazole (=3-(2,4-dichlorophenyl)-6-fluoro-2-(1H-1,2,4-triazol-1-yl)quinazolin) or IIB) 4,5-dimethyl-N-2-propenyl-2-(trimethylsilyl)-3-thiophencarboxamide which is especially suitable in the control and prevention of disease infestation on seed.

9 Claims, No Drawings

PESTICIDAL COMPOSITIONS

The present invention relates to fungicidal mixtures having synergistically enhanced action and to methods of using such mixtures in crop protection, especially in the control and prevention of disease infestation on seed.

The mixtures according to the invention comprise at least two fungicidally active components together with a suitable carrier material, wherein component I is I) fludioxonil (=4-(2,2-difluoro-1,3-benzodioxol-4-yl) pyrrole-3-carbonitrile; The Pesticide Manual, 10th. edition, 1994, 326); and wherein component II is IIA) fluquinconazole (=3-(2,4-dichlorophenyl)-6-fluoro-2-(1H-1,2,4-triazol-1-yl)quinazolin-4(3H)-one; The Pesticide Manual, 10th. edition, 1994, 338) or IIB) 4,5-dimethyl-N2-propenyl-2-(trimethylsilyl)-3-thiophencarboxamide (Proceedings Brighton Conf. 1998, p. 343, MON65500).

The active ingredient mixtures I+II according to the invention have very advantageous properties for protecting plants against disease infestation, especially in the control and prevention of disease infestation on seed.

The synergistically enhanced action of mixtures of components I and II manifests itself, for example, in lower disease infestation, lower rates of application, a longer duration of action and altogether higher crop yields. Such enhancements were not to be expected from the sum of the actions of the individual components.

The weight ratio is selected as to give a synergistic action. In general, the weight ratio I:II is from 100:1 to 1:100.

Advantageous mixing ratios of the two active ingredients are

I:IIA=1:20 to 20:1, preferably 1:15 to 15:1, most preferably 1:5 to 5:1; or

I:IIB=1:20 to 20:1, preferably 1:5 to 5:1, most preferably 1:2 to 2:1.

The above mentioned mixtures may be mixed with other pesticides, preferably fungicides, resulting in some cases in unexpected synergistic activities.

The active ingredient mixtures in question can be used to inhibit or destroy the micro-organisms which occur on plants or on parts of plants (the fruit, blossom, leaves, stems, tubers or roots) of different crops of useful plants, while at the same time parts of plants that grow later are also protected against such microorganisms. They can also be used as dressings in the treatment of plant propagation material, especially seed (fruit, tubers, grains) and plant cuttings (e.g. rice), to provide protection against fungus infections as well as against phytopathogenic fungi which occur in the soil. The active ingredient mixtures according to the invention are distinguished by the fact that they are especially well tolerated by plants and are environmentally friendly.

The active ingredient mixtures are effective against phytopathogenic fungi belonging to the following classes: Ascomycetes (e.g. Venturia, Podosphaera, Erysiphe, Monilinia, Mycosphaerella, Uncinula, *Gaeumannomyces graminis*); Basidiomycetes (e.g. the genus Hemileia, Rhizoctonia, Puccinia); Fungi imperfecti (e.g. Botrytis, Helminthosporium, Rhynchosporium, Fusarium, Septoria, Cercospora, Alternaria, Pyricularia and *Pseudocercosporella herpotrichoides*); Oomycetes (e.g. Phytophthora, Peronospora, Bremia, Pythium, Plasmopara).

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). This list does not represent any limitation.

The active ingredient mixtures according to the invention are especially advantageous for seed treatment of cereals (wheat, barley, rye, oats, rice, sorghum and related crops), in particular seed of wheat and barley.

The mixtures of compounds of formulae I and II are normally used in the form of compositions. The compounds of formulae I and II can be applied to the area or plant to be treated either simultaneously or in succession on the same day, if desired together with further carriers, surfactants or other application-promoting adjuvants customarily employed in formulation technology.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

A method of applying an active ingredient mixture comprising at least one of each of the active ingredients I and II is application to the parts of the plants that are above the soil, especially to the leaves (foliar application). The frequency and rate of application depend upon the biological and climatic living conditions of the pathogen. The active ingredients can, however, also penetrate the plant through the roots via the soil or via the water (systemic action) if the locus of the plant is impregnated with a liquid formulation (e.g. in rice culture) or if the substances are introduced in solid form into the soil, e.g. in the form of granules (soil application). In order to treat seed, the compounds of formulae I and II can also be applied to the seeds (coating), either by impregnating the tubers or grains with a liquid formulation of each of the active ingredients in succession, or by coating them with an already combined wet or dry formulation. In addition, in special cases, other methods of application to plants are possible, for example treatment directed at the buds or the fruit trusses.

The compounds of the combination are used in unmodified form or, preferably, together with the adjuvants conventionally employed in formulation technology, and are therefore formulated in known manner e.g. into emulsifiable concentrates, coatable pastes, directly sprayable or dilutable solutions, dilute emulsions, wettable powders, soluble powders, dusts, granules, or by encapsulation in e.g. polymer substances. As with the nature of the compositions, the methods of application, such as spraying, atomizing, dusting, scattering, coating or pouring, are chosen in accordance with the intended objectives and the prevailing circumstances. Advantageous rates of application of the active ingredient mixture are generally from 50 g to 2 kg a.i./ha, especially from 100 g to 1000 g a.i./ha, more especially from 250 g to 700 g a.i./ha. In the case of the treatment of seed, the rates of application are from 0.5 g to 500 g, preferably from 1 g to 100 g, most preferably from 5 g to 50 g a.i. per 100 kg of seed.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. especially dolomite or pulverized plant residues.

Depending upon the nature of the compounds of formulae I and II to be formulated, suitable surface-active compounds are non-ionic, cationic and/or anionic surfactants having good emulsifying, dispersing and wetting properties. The term "surfactants" will also be understood as comprising mixtures of surfactants. Particularly advantageous application-promoting adjuvants are also natural or synthetic phospholipids of the cephalin and lecithin series, e.g. phosphatidylethanolamine, phosphatidylserine, phosphatidylglycerol and lysolecithin.

The agrochemical compositions normally comprise 0.1 to 99%, especially 0.1 to 95%, compounds of formulae I and II, 99.9 to 1%, especially 99.9 to 5%, of a solid or liquid adjuvant and 0 to 25%, especially 0.1 to 25%, of a surfactant.

Whereas commercial products will preferably be formulated as concentrates, the end user will normally employ dilute formulations.

The Examples which follow serve to illustrate the invention, "active ingredient" denoting a mixture of compound I and compound II in a specific mixing ratio.

FORMULATION EXAMPLES

| Wettable powders | a) | b) | c) |
|---|---|---|---|
| active ingredient [I:II = 1:3(a), 1:2(b), 1:1(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Dusts | a) | b) | c) |
|---|---|---|---|
| active ingredient [I:II = 1:6(a), 1:2(b), 1:10(c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Coated granules | |
|---|---|
| active ingredient (I:II = 1:10) | 8% |
| polyethylene glycol (mol. wt. 200) | 3% |
| kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:II = 1:8) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

A synergistic effect exists, for example, whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20–22; 1967): ppm=milligrams of active ingredient (=a.i.) per litre of spray mixture X=% action by active ingredient I using p ppm of active ingredient Y=% action by active ingredient II using q ppm of active ingredient.

According to Colby, the expected (additive) action of active ingredients I+II using p+q ppm of active ingredient is $$E = X + Y - \frac{X \cdot Y}{100}.$$

If the action actually observed (O) is greater than the expected action (E), then the action of the combination is superadditive, i.e. there is a synergistic effect.

Example B-1
Action Against *Puccinia graminis* on Wheat 6 days after sowing, wheat plants are sprayed to drip point with an aqueous spray mixture of the active ingredient mixture prepared from a wettable powder formulation. The treated plants are infected 24 hours later with a uredospore suspension of the fungus. After an incubation time of 48 hours in a climatic chamber at 95 to 100% relative humidity and 20–22° C., the plants are stood at 22° C. in a greenhouse. Fungus infestation is evaluated 12 days after infection.

Example B-2
Action Against *Helminthosporium gramineum* on Barley: Seed Treatment Barley seeds are contaminated with a spore suspension of the fungus and left to dry. The contaminated seeds are dressed with a suspension of the test substance. After two days, the seeds are placed on suitable agar dishes and, after a further four days, the development of the fungal colonies around the seeds is evaluated. The number and size of the fungal colonies are used to evaluate the test substance.

Example B-3
Action Against *Fusarium nivale* in Rye: Seed Treatment

Rye seeds of the Tetrahell variety naturally infected with Fusarium nivale are dressed in a roller mixer with the test fungicides. The infected and treated rye is sown in October in the open with a seeder in plots 3 metres long and in 6 rows. Three replicates are carried out with each concentration. The test plants are cultivated under normal field conditions, harvested and dryed.

Example B-4
Action Against *Venturia inequalis* on Apples

Apple cuttings with fresh shoots 10 to 20 cm long are sprayed to drip point with a spray mixture prepared from a wettable powder formulation of the test mixture. The plants are infected 24 hours later with a conidia suspension of the fungus. The plants are then incubated for 5 days at 95 to 100% relative humidity and stood in a greenhouse for further 10 days at 20 to 24° C. Evaluation of the fungal infestation is made 12 days after infection.

Example B-5
Action Against *Erysiphe graminis* on Barley

Barley plants about 8 cm in height are sprayed to drip point with a spray mixture prepared from a wettable powder formulation of the test mixture, and the treated plants are dusted with conidia of the fungus 3 to 4 hours later. The infected plants are stood in a greenhouse at 22° C. Evaluation of the fungal infection is made 12 days after infection.

Example B-6
Action Against *Gaeumannomyces graminis* var. *tritici*

Gaeumannomyces graminis var. tritici, strain 333 (Novartis culture collection) is cultivated under sterile conditions on PDA-medium. PDA-medium (DIFCO) is prepared as described by the manufacturer: 39 g in 1 L $H_2O$ bidest., autoclaved at 121° C. for 20 min, and cooled down to 55° C. Petri dishes with 3 compartments (GREINER, 94/15, Item-Nr. 637102) are used. First, each compartment from one dish is filled with 500 μl of a solution of a test compound or mixture of test compounds and 4500 μl of PDA-medium. To obtain the final concentrations, the test solutions are diluted with sterile $H_2O$ bidest. Each petri dish contains 3 replicates for one concentration of the test compound or compounds. After mixing and drying on a shaker, one agar disc, taken with a cork borer from an actively growing colony, is placed upside down onto the agar surface of each compartment. After incubation for one week at 20° C., in the dark, the radius of mycelium growth is measured, and converted in % activity.

Evaluation:

The radius of the mycelial growth is measured, the activity of the test compound or compounds is calculated relative to the growth on the control agar. The calculation of the expected activity is done according to the Colby formula.

Results:

| fludioxonil [mg a.i./l] | MON 65500 [mg a.i./l] | mixing ratio | expected activity [%] | observed activity [%] |
|---|---|---|---|---|
| 0.05 | | | | 0 |
| 0.005 | | | | 0 |
| | 0.05 | | | 84 |
| | 0.01 | | | 75 |
| | 0.005 | | | 71 |
| 0.05 | 0.005 | 10:1 | 71 | 84 |
| 0.05 | 0.01 | 5:1 | 75 | 92 |
| 0.005 | 0.01 | 1:2 | 75 | 88 |
| 0.005 | 0.05 | 1:10 | 84 | 98 |

"bold": mixture according to the invention

| fludioxonil [mg a.i./l] | fluquinconazole [mg a.i./l] | mixing ratio | expected activity [%] | observed activity [%] |
|---|---|---|---|---|
| 5 | | | | 12 |
| 0.1 | | | | 0 |
| | 1 | | | 97 |
| | 0.5 | | | 95 |
| 5 | 0.5 | 10:1 | 95 | 100 |
| 0.1 | 0.5 | 1:5 | 95 | 100 |
| 0.1 | 1 | 1:10 | 97 | 100 |

"bold": mixture according to the invention

What is claimed is:

1. An agrochemical composition, comprising synergistic fungicidally effective amounts of at least two active ingredient components together with a suitable carrier, wherein component I is I) fludioxonil (=4-(2,2-difluoro-1,3-benzodioxol-4-yl)pyrrole-3-carbonitrile) and wherein component II is IIA) fluquinconazole (=3-(2,4-dichlorophenyl)-6-fluoro-2-(1H-1,2,4-triazol-1-yl)quinazolin) or IIB) 4,5-dimethyl-N-2-propenyl-2-(trimethylsilyl)-3-thiophencarboxamide.

2. A composition according to claim 1, wherein component II is IIA) fluquinconazole.

3. A composition according to claim 1, wherein component II is IIB) 4,5-dimethyl-N-2-propenyl-2-(trimethylsilyl)-3-thiophencarboxamid.

4. A composition according to claim 1, wherein the ratio by weight of I:II is 1:100 to 100:1.

5. A composition according to claim 1, wherein the ratio by weight of I:II is 1:20 to 20:1.

6. A method for protecting plants against plant diseases by treating the plants, parts of plants or their surroundings with a synergistic fungicidally effective combined amount of the composition comprising a component I and a component II according to claim 1, in any desired sequence or simultaneously.

7. A method according to claim 6, wherein seed is treated.

8. A method according to claim 6, wherein seed of cereals is treated.

9. Cereal seeds which have been treated in accordance with claim 8.

* * * * *